United States Patent [19]
Jeffress

[11] Patent Number: 4,706,598
[45] Date of Patent: Nov. 17, 1987

[54] DETACHABLE HANDLE EXTENDER AND TRANSVERSE ENLARGER FOR USE WITH LONGITUDINALLY RECIPROCABLE HANDLES OR PLUNGERS BY HANDICAPPED PERSONS

[76] Inventor: William L. Jeffress, 740 Elm, Emporia, Kans. 66801

[21] Appl. No.: 858,106

[22] Filed: May 1, 1986

[51] Int. Cl.$^4$ .............................................. B25G 3/12
[52] U.S. Cl. ................................. 16/112; 16/114 R; 16/253; 16/332; 16/DIG. 25; 403/344
[58] Field of Search ................ 16/114 R, 114 A, 115, 16/121, 319, 321, 332, 252, 253, DIG. 24, DIG. 25, DIG. 30, DIG. 40; 74/544, 546; 403/344; 251/293; 417/511; 15/145

[56] References Cited
U.S. PATENT DOCUMENTS

| | | | |
|---|---|---|---|
| 2,112,658 | 3/1938 | Rathbun | 16/114 R X |
| 2,319,147 | 5/1943 | Mason | 16/114 R |
| 2,349,887 | 5/1944 | Selberg | 16/114 R X |
| 2,377,953 | 6/1945 | Matton | 16/114 R |
| 2,995,998 | 8/1961 | Howland | 16/114 A X |
| 4,035,865 | 7/1977 | McRae et al. | 16/114 R |
| 4,255,830 | 3/1981 | Wilson | 16/114 R |
| 4,266,320 | 5/1981 | Grant | 16/114 R |
| 4,504,087 | 3/1985 | Pennington | 16/114 R X |

Primary Examiner—Fred Silverberg
Attorney, Agent, or Firm—Robert E. Breidenthal

[57] ABSTRACT

A handle especially convenient for arthritics or handicapped persons that includes two hingedly connected sections that close together to mate with and engage an object received between ends of the sections remote from their hinged connection. When the sections are closed, the hinged ends thereof define a handle. The sections can be releasably secured in their closed relation.

1 Claim, 9 Drawing Figures

DETACHABLE HANDLE EXTENDER AND TRANSVERSE ENLARGER FOR USE WITH LONGITUDINALLY RECIPROCABLE HANDLES OR PLUNGERS BY HANDICAPPED PERSONS

BACKGROUND OF THE INVENTION

1. Field of the Invention

The present invention relates to apparatus for aiding persons who must manipulate devices with crippled hands (hands that are malformed, dismembered or afflicted with arithritis or the like), and more particularly pertains to apparatus of such character that is especially well suited to enable a person with a crippled hand to actuate the plunger of an air pump such as assembled or affixed to a liquid fuel tank for pressurizing the latter. Such fuel systems are used extensively as, for example, with gasoline cook stoves, mantle-type gasoline lanterns, etc. Such examples serve to show how a crippled person otherwise capable of going camping by himself may be inhibited from doing so, or feel himself to be too great a burden upon any prospective camping companion.

2. Description of Related Art

Numerous proposals have heretofore been made with respect to providing hand manipulated devices with handles or configurations such that they can be more conveniently operated or actuated by persons afflicted with arthritis for example.

U.S. Pat. No. 4,035,865 which issued July 19, 1977, to Lucy McRae et al discloses a ball-shaped structure that enables a person with arthritis to manipulate eating utensils and the like.

U.S. Pat. No. 2,112,658 which issued Mar. 29, 1938, to Rathburn discloses a toothbrush provided with an enlarged handle extension that alternatively serves as a receptacle for the toothbrush.

U.S. Pat. No. 1,143,360 which issued June 15, 1915, to Chorvath et al discloses a door handle attachment intended for another purpose, but which it can be assumed may be useful insofar as more convenient utilization by a person with a crippled hand is concerned.

U.S. Pat. No. 4,255,830 which issued Mar. 17, 1981, to G. Kevin Wilson recognizes a specific need met by the present invention is that it discloses a D-shaped handle adapted to be connected to the free end of a pump plunger for the liquid fuel supply tank of a lantern or stove.

SUMMARY OF THE INVENTION

The paramount object of the present invention is to provide a handle extension that can be detachably secured to a free end of a device actuator that may easily be manipulated by use of a crippled hand to force the actuator toward and away from the device.

An ancillary object of the invention is to provide such a handle extension such that most persons can, without assistance from others, attach and detach the same from a device actuator.

The foregoing objectives are attained by providing an improved handle for facilitating the handling of devices otherwise difficult or impossible to handle by persons having hands that have been dismembered or that are affected by arthritis and the like, said improved handle comprising an elongated body that includes a grasping portion adapted to be grasped by a crippled hand at one end, with such body also including a device engaging portion at its other end that is adapted for engagement with a device to be handled, said body being comprised of two sections each of which extend the length of the body, means connecting the sections together at said one end of the body for swinging movement of the sections toward and away from each other between a closed position such that adjacent faces of the sections seat against each other and an open position wherein the adjacent faces of the sections diverge and are spaced apart at said other end of the body, said sections having end portions corresponding to said device engaging portion of the body, with said end portions of the sections being provided with recesses in their adjacent faces adapted to receive in mating fashion and to engage a device therebetween when the sections are swung to their closed position, and means for releasably retaining the sections in their closed position.

BRIEF DESCRIPTION OF THE DRAWING

The invention will be fully understood in the light of the following description of a preferred embodiment of the invention, such description being given in conjunction with the accompanying drawings illustrative of the same, wherein.

DESCRIPTION OF THE PREFERRED EMBODIMENT

Figure 1:
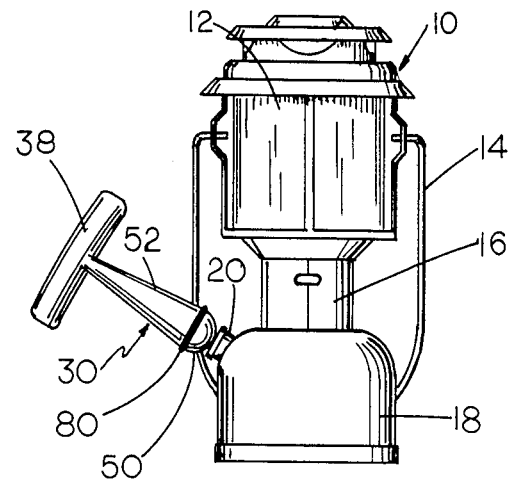
FIG. 1 is an elevational view of a liquid-fueled lantern inclusive of its fuel tank and showing the hand extender of this invention attached to the plunger of the air pump incorporated within the fuel tank for pressurizing the latter.

Referring now to the drawings wherein like numerals designate like parts throughout the various views, the reference numeral 10 designates generally a conventional mantle-type gasoline lantern. The lantern 10 includes a conventional upper light emitting means 12 provided with a handle or bail 14. The light emitting means 12 is conventionally mounted upon a conventional lantern control means 16 that is carried on the top of a conventional air-tight liquid fuel tank 18. The tank is conventionally provided with a conventional filling opening having a removable closure cap, not shown.

Also, conventionally, the fuel tank 18 incorporates reentrant structure constituting an air pump for pressurizing the interior of the tank 18. Only a portion of the air pump projects outwardly from and is visible on the outside of the tank, and such conventional exposed or visible portion of the air pump is indicated at 20. The pump is indicated at 20. The pump conventionally includes an elongated plunger 22 that can be reciprocatingly extended from the tank 18 and the re-entrant and concealed pump structure within the tank 18.

Figure 2:
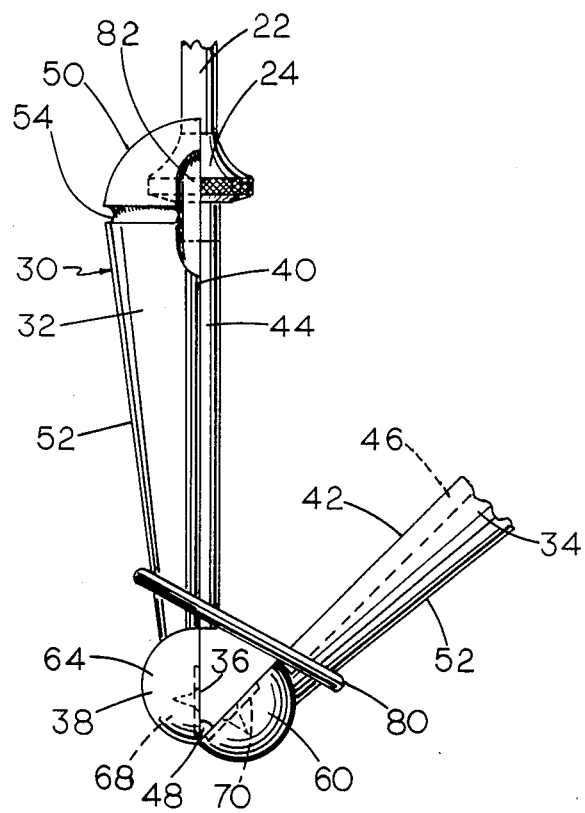
FIG. 2 is an enlarged fragmentary view showing an intermediate stage of attachment to a fragmentary showing of the conventional air pump plunger.
Figure 3:
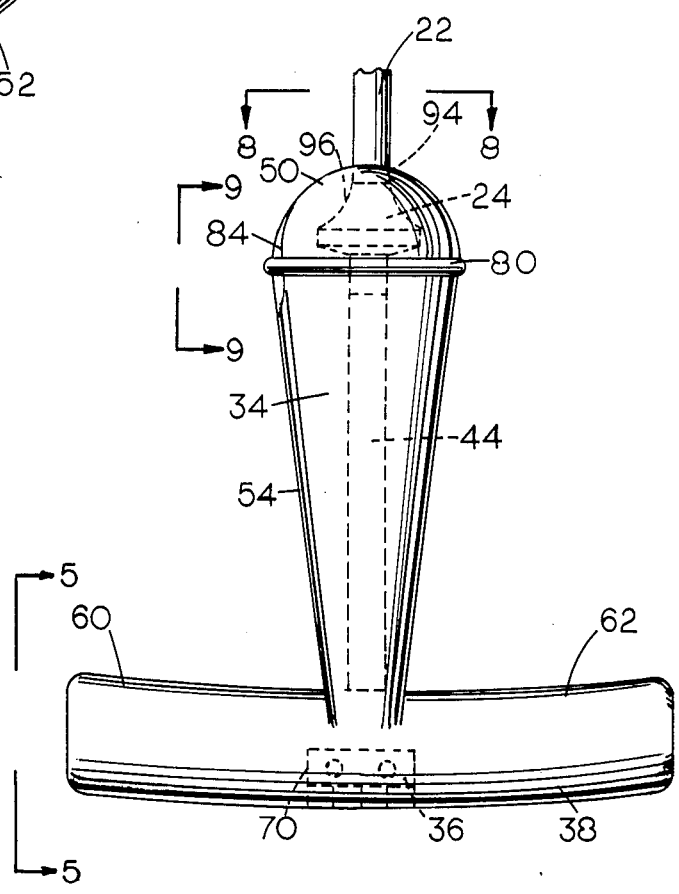
FIG. 3 is a side view of the handle extender showing the same attached to a fragmentary showing of the pump plunger; this view being taken from a plane parallel to the axis of the pivotal connection of the handle sections, with hidden details and an alternative position of the retainer ring being shown in dashed outline.
Figure 4:
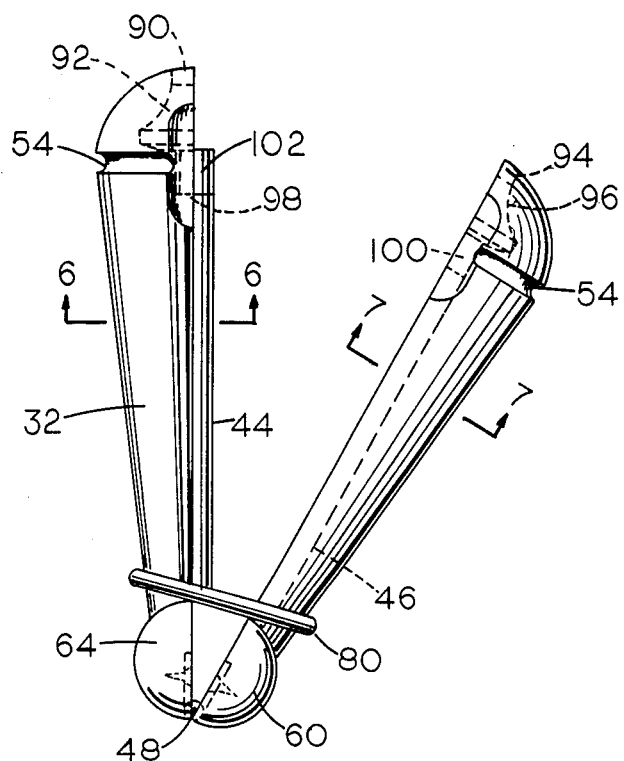
FIG. 4 is generally similar to FIG. 2, and shows the entire handle extension without the pump plunger; this view being taken from a plane normal to the axis of the pivotal connection of the handle sections.
Figure 5:
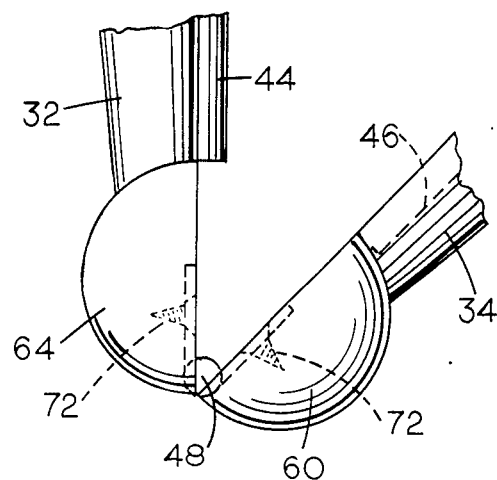
FIG. 5 is an enlarged fragmentary and sectional view illustrating the pivotally connected end of the handle extender, the view being taken upon the plane of the section line 5—5 in FIG. 3 with the sections being pivotally opened.
Figure 6:
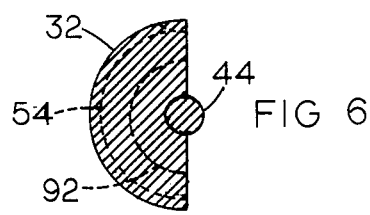
FIGS. 6 and 7 are sectional views taken respectively upon the planes of the section lines 6—6 and 7—7 of FIG. 4.
Figure 7:
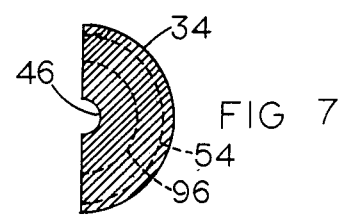
Figure 8:
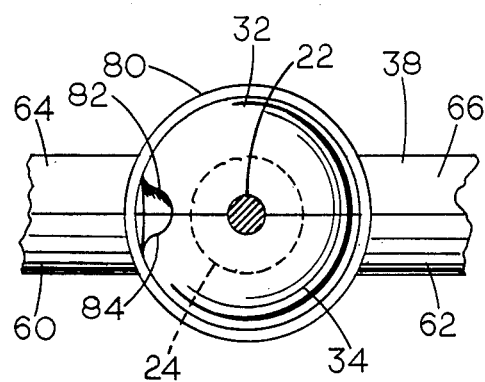
FIG. 8 is a fragmentary sectional view taken upon the plane of the section line 8—8 in FIG. 3; and, FIG. 9 is a fragmentary elevational view taken from the plane of the line 9—9 in FIG. 3.
Figure 9:
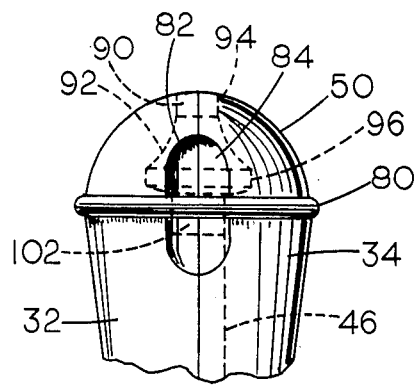

The plunger is designated at 22 and as best shown in FIGS. 2 and 3 has a conventional radially enlarged free end portion 24 of a configuration constituting a surface of revolution about the axis of the longitudinal extent of the plunger 22.

The plunger 22, including its enlarged head or end 24, is conventionally provided with a longitudinally extending passageway or vent, not shown, and conventional structure, also not shown, is provided to interconnect the inner end of the plunger 22 and other internal components of the pump 20 so that the plunger 22 can be secured on clockwise turning of the latter.

The structure thus far described is entirely conventional and is and has for many years been in very widespread public use, and indeed, it is believed that any overnight camper not familiar with the described lantern is a rarity.

Unfortunately, the headed plunger 24 presents quite a difficulty to a person with a crippled hand. Such difficulty resides in the fact that the head 24, while quite adequate and convenient to a normal hand, is small and is difficult for the crippled hand to grip and to forcefully reciprocate the same quite a few times to pressurize the tank 18 sufficiently.

The present invention is provided for the express purpose of enabling hands to surmount the difficulties alluded to above.

The present invention preferably takes the form of the handle extension designated generally at 30. The handle extension 30 is comprised of two elongated sections 32 and 34 which are hingedly connected at one end by a hinge 36.

The handle sections 32 and 34 can be preferably molded or formed of any suitable synthetic resin, though they can be cast of aluminum or diecast of a zinc alloy. Nylon is well suited as a material.

The handle preferably has an overall T-shaped configuration with the handle portion of the structure or cross piece 38 of the "T" being at the hinged end of the sections 32 and 34 as clearly shown in FIG. 3.

Except as hereinafter specifically pointed out, the sections 30 and 32 are mirror images of each other and have opposed planar faces 40 and 42 that seat together at the plane of symmetry when the handle extension 30 is in its closed or operative condition.

Extending longitudinally along the face 40 of section 30 is a central tongue that is received in a groove 46 centrally extending along the longitudinal extent of the section face 42. The tongue and groove connection 44 and 46 between the sections 30 and 32 serves to guide closure of the sections 30 and 32 and to limit or prevent relative movement of the sections 30 and 32 other than about the axis 48 of the hinge 36.

Except for the handle portion 38, the external configuration of the handle extender 30 when closed or in its operative condition is a surface of revolution about the central longitudinal axis and includes a generally hemispherical end portion 50 that merges with a monotonically tapering portion 52 that extends to the handle portion 38, with a peripheral groove 54 being provided at the juncture of the portions 50 and 52.

In the preferred construction, the handle portion or cross piece of the "T-shape" configuration lies in the aforementioned plane of symmetry so that the section 34 includes oppositely extending projections 60 and 62 defining the section 34 half of the handle portion 38, with the section 32 half of the handle portion 38 being defined by two complementary projections 64 and 66.

The hinge 36 is conventional and includes hinge plates 68 and 70 that are hingedly connected as shown to define the hinge axis 48. The sections 32 and 34 are recessed as shown to receive the plates 68 and 70 and their hinge connection, and the plates are secured by screw means 72.

If desired or deemed expedient, it will be manifest to those skilled in the art that the handle portion 38 can be oriented as pleased such as normal to rather than parallel to the hinge axis 48 as shown.

Means are provided for releasably retaining the sections 32 and 34 in their closed or operative position. Such means includes the groove 54 and a resilient ring or band 80 that is received in the groove 54 to snugly embrace the sections 32 and 34. The band 80 can be resiliently extended so as to be removed from the groove 54 and preferably moved toward the handle portion 38 that will preclude inadvertent dislodgment from the handle extender 30. Movement of the band 80 towards the hinge axis 48 and about the smaller periphery of the structure as shown in full lines in FIG. 2 and in dashed outline in FIG. 3, enables the sections 32 and 34 to be pivoted apart from their closed or clamping relationship.

Recesses 82 and 84 are provided in the sections 32 and 34 to underlie the groove 54, whereby a finger or other object may be inserted to facilitate extraction of the resilient retention band 80 from the groove 54.

The adjacent faces of the ends of the sections 32 and 34 remote from the handle portion 38 are appropriately recessed to receive therein a short portion of the cylindrical extent of the plunger 22 and the enlargement 24 thereon. Section 32 has communicating recesses 90 and 92 that respectively accommodate the cylindrical portion 22 and the enlarged portion 24 of the pump plunger or pump piston actuator. Similarly the section 34 has recesses 94 and 96. The recesses 94 and 96 are mirror images of the recesses 90 and 92. The recesses are so oriented as to be concentric with longitudinal extent of handle extender 30 and so that the latter will be an axial extension of the plunger 22 when the latter and its enlargement 24 are received in the recesses.

While the fit of plunger 22 and its enlargement 24 in the recesses are sufficiently snug as to afford little if any air communication between the plunger vent and ambient atmosphere, the fit nonetheless enables relative axial rotation so that the user can orient the handle portion 38 relative to the lantern 10 as may be most convenient for him.

If desired or deemed expedient, the sections 32 and 34 can be provided with opposing recesses 98 and 100. The recess 98 is intermediate the tongue 44 and the recess 92 and contains a sealing gasket or sealing washer 102 that is received in recess 100 when the sections 32 and 34 are in clamping engagement with each other; the recess 100 being disposed between the groove 46 and the recess 96 as shown.

The fabrication and use of the handle extender 30 will be readily apparent, especially as it is obvious that the handle portion 38 is far more susceptible to manipulation than the enlarged plunger head 24.

In most instances a person with a crippled hand can manage to position and remove the retainer ring or band and thereby attach and detach the handle extender 30.

The handle extender 30 can usually be used interchangeably with the gasoline lantern and liquid fueled camp stoves, as the pump plungers of the latter are quite similar to those of the lanterns.

Having now fully described the invention and its practice, attention is invited to the appended claims to ascertain the actual scope of the invention.

I claim:

1. An improved handle for enabling persons having hands that have been dismembered or that are affected by arthritis and the like to handle devices that must be longitudinally reciprocated, said improved handle comprising an elongated body that includes a transversely extending grasping portion at one end that is adapted to be grasped by a crippled hand, with said body also including a device engaging portion at its other end that is adapted for engagement with an end of a longitudinally reciprocable device that is to be handled, said body being comprised of two sections each of which extend the length of the body, means connecting the sections together at said one end of the body for swinging movement of the sections toward and away from each other about an axis that is normal to the longitudinal extent of the body between a closed position such that adjacent faces of the sections seat against each other and an open position wherein the adjacent faces of the sections diverge and are spaced apart at said other end of the body, said sections having end portions corresponding to said device engaging portion of the body, with said end portions of the sections being provided with recesses in their adjacent faces adapted to receive in mating fashion and to engage a device therebetween when the sections are swung to their closed position, means outside the body for releasably retaining the sections in their closed position, said body having a transverse peripheral extent that increases monotonically from the grasping portion to the device engaging portion, said means for releasably retaining the sections closed comprising a resilient band encircling the body intermediate the grasping and device engaging portions, said device engaging portion of the body having a peripheral retention groove thereabout adapted to tautly receive the resilient band therein, with said device engaging portion having a recess therein that communicates with said retention groove, thereby to facilitate dislodgment of the band from the retention groove.

* * * * *